(12) United States Patent
Hondroulis et al.

(10) Patent No.: US 9,404,840 B2
(45) Date of Patent: Aug. 2, 2016

(54) PORTABLE GRAVEL IMPACT DAMAGE SIMULATOR

(71) Applicant: Film Sales Tools, Inc., Baltimore, MD (US)

(72) Inventors: Emmanuel Hondroulis, Towson, MD (US); James Hondroulis, Hunt Valley, MD (US); Marian Giorgakis, Abingdon, MD (US); Stephen Novak, Perry Hall, MD (US); Michael Tutchton, Baltimore, MD (US); John Diamond, Perry Hall, MD (US)

(73) Assignee: Film Sales Tools, Inc., Baltimore, CA (US)

( * ) Notice: Subject to any disclaimer, the term of this patent is extended or adjusted under 35 U.S.C. 154(b) by 224 days.

(21) Appl. No.: 14/313,262

(22) Filed: Jun. 24, 2014

(65) Prior Publication Data

US 2014/0373598 A1 Dec. 25, 2014

Related U.S. Application Data

(60) Provisional application No. 61/838,470, filed on Jun. 24, 2013.

(51) Int. Cl.
*G01N 3/30* (2006.01)
*G01N 3/56* (2006.01)
(Continued)

(52) U.S. Cl.
CPC .............. *G01N 3/30* (2013.01); *G01M 99/007* (2013.01); *G01N 3/567* (2013.01); *G01N 2033/0096* (2013.01)

(58) Field of Classification Search
CPC ........... G01N 3/30; G01N 3/56; G01N 3/567; G01N 3/62; G01N 2233/0096; G01M 99/007
See application file for complete search history.

(56) References Cited

U.S. PATENT DOCUMENTS 6,174,225 B1 * 1/2001 Becker .................... B24C 1/003
451/39
6,679,095 B1 1/2004 Grossman et al.
(Continued)

FOREIGN PATENT DOCUMENTS

DE 10231802 A1 * 2/2004 ............. G01N 3/567
IT EP 0434633 A1 * 6/1991 ............. G01N 3/567
(Continued)

OTHER PUBLICATIONS

"Gravelometer Test" screenshots, YouTube video at http://www.youtube.com/watch?v=5hv1E8db10k, Nov. 21, 2008.

*Primary Examiner* — Nguyen Ha
(74) *Attorney, Agent, or Firm* — Alan G. Towner, Esq.; Pietragallo Gordon Alfano Bosick & Raspanti, LLP

(57) ABSTRACT

An improved device for simulating gravel impact damage on panels, such as protected and unprotected areas of painted vehicle panels, is disclosed. The gravel impact damage simulator includes an enclosure, a gravel inlet port having an extension spout, a motor-driven rotatable impeller below the inlet port, a downwardly angled baffle between the inlet port and the impeller, and a test panel slot through which a test panel may be inserted into the enclosure. During operation, gravel is introduced through the extension spout and inlet port. The gravel drops into the angled baffle, where it is directed toward the rotating impeller. The rotating impeller strikes the gravel and projects it toward the test panel.

20 Claims, 4 Drawing Sheets

(51) Int. Cl.
  *G01M 99/00* (2011.01)
  *G01N 33/00* (2006.01)

(56) References Cited

U.S. PATENT DOCUMENTS

| | | |
|---|---|---|
| 2002/0095983 A1 | 7/2002 | Heil et al. |
| 2002/0104371 A1* | 8/2002 | Gitis ................... G01N 3/46 73/81 |
| 2002/0182988 A1* | 12/2002 | Williams ............... B24C 9/00 451/89 |
| 2004/0092215 A1* | 5/2004 | Burgel .................. G01N 3/567 451/75 |
| 2005/0081599 A1* | 4/2005 | Wortmann ............. G01N 3/56 73/7 |
| 2006/0150710 A1* | 7/2006 | Moyse .................. G01N 19/02 73/7 |

FOREIGN PATENT DOCUMENTS

| | | | |
|---|---|---|---|
| JP | 57094633 A * | 6/1982 | ............... G01N 3/30 |
| JP | 1997-216137 | 3/1997 | |
| WO | 9939179 | 8/1999 | |

\* cited by examiner

PORTABLE GRAVEL IMPACT DAMAGE SIMULATOR

CROSS-REFERENCE TO RELATED APPLICATION

This application claims the benefit of U.S. Provisional Patent Application Ser. No. 61/838,470 filed Jun. 24, 2013, which is incorporated herein by reference.

FIELD OF THE INVENTION

The present invention relates to gravel impact damage simulators, and more particularly relates to portable simulators that can demonstrate gravel impact damage on protected and unprotected areas of painted test panels.

BACKGROUND INFORMATION

Vehicles such as cars and trucks are susceptible to damage from gravel and other road debris. Various protective measures have been taken to reduce paint chipping and other vehicle damage, including the application of protective urethane sheets or films over the areas of vehicles that are most likely to be damaged. The effectiveness of such protective sheets and films may be demonstrated by projecting gravel against protected and unprotected areas of a painted panel, and comparing the resulting damage in the protected and unprotected areas.

Standard tests have been developed to measure paint chipping resistance. For example, the ASTM Standard Test Method for Chipping Resistance of Coatings, ASTM D3170-12, is a test procedure where standardized road gravel is projected within an enclosed cabinet or module by means of a controlled air blast onto a test specimen. In accordance with the ASTM D3170-12 test, air that has been pressurized to 70 psi is released through a valve and is used to project the gravel toward the test specimen. The test specimen may then be analyzed to determine the amount of chipping of the painted surface.

SUMMARY OF THE INVENTION

The present invention provides an improved device for simulating gravel impact damage on panels, such as protected and unprotected areas of painted vehicle panels.

An aspect of the present invention is to provide a gravel impact damage simulator comprising: an enclosure; a gravel inlet port extending through a wall of the enclosure, wherein the gravel inlet port comprises an extension spout extending from the wall of the enclosure; a motor-driven rotatable impeller below the inlet port within the enclosure, wherein the rotatable impeller has an axis of rotation that is offset at an angle measured from a vertical direction; a downwardly angled baffle positioned in a gravel flow path between the gravel inlet port and the rotatable impeller; and a test panel slot through a wall of the enclosure structured and arranged to receive a test panel to be positioned in the gravel flow path.

Another aspect of the present invention is to provide test panels for use in such a gravel impact damage simulator A further aspect of the present invention is to provide a method of using such a gravel impact damage simulator.

These and other aspects of the present invention will be more apparent from the following description.

BRIEF DESCRIPTION OF THE DRAWINGS

In FIG. 6, the top of the simulator has been removed to show the internal components thereof.

DETAILED DESCRIPTION

Figure 1:
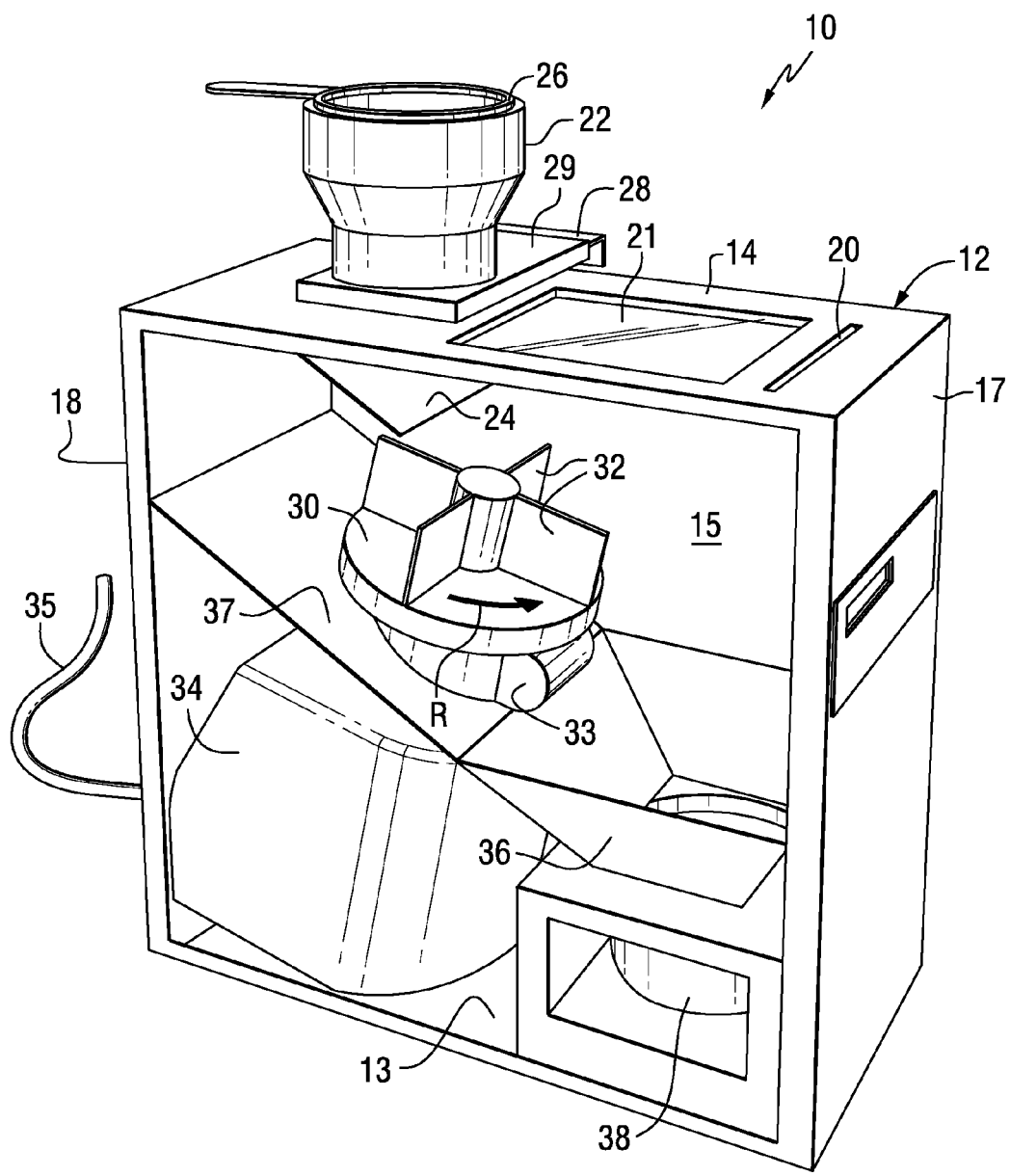
FIG. 1 is an isometric view of a gravel impact damage simulator in accordance with an embodiment of the present invention with its side panel removed to show the internal components of the simulator.
Figure 2:
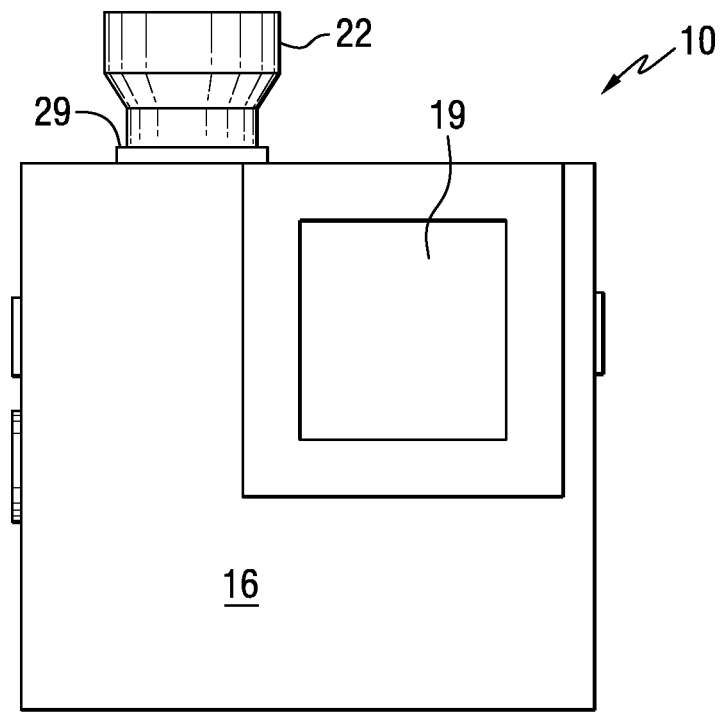
FIGS. 2 and 3 are side views of the gravel impact damage simulator of FIG. 1.
Figure 3:
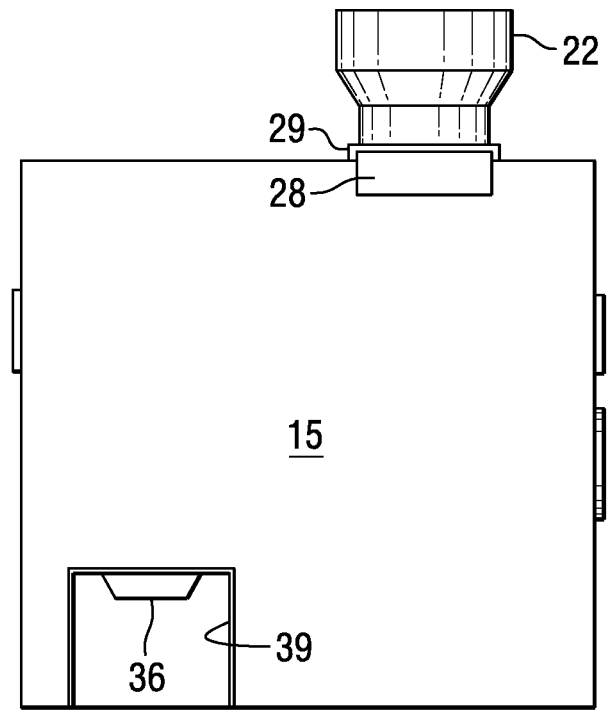

FIGS. 1-6 illustrate various features of a gravel impact damage simulator 10 in accordance with an embodiment of the present invention. The simulator 10 includes an enclosure 12 having a base 13, a top 14, side walls 15 and 16, and end walls 17 and 18. As shown most clearly in FIGS. 1, 4 and 5, a slot 20 is provided in the top 14 for receiving a test panel 40, as more fully described below. A top window 21 is provided in the top 14 of the enclosure 12. An extension spout 22 having a central opening is mounted above an inlet port through the top 14 of the enclosure 12. The extension spout 22 has an upper cylindrical section, a lower cylindrical section of smaller diameter than the upper section, and a conical section connecting the upper and lower cylindrical sections. The height of the extension spout 22 is typically at least as large as the diameter of the inlet opening through the top 14.

As shown most clearly in FIGS. 1, 4 and 5, an angled baffle 24 is secured to the top 14 of the enclosure 12 and includes a downwardly angled ramp surface that directs the flow of gravel and prevents unwanted backward ejection of the gravel during operation of the gravel impact damage simulator 10, as more fully described below. The angled baffle 24 has a sloped surface with a slope angle typically ranging from 10 to 60 degrees, for example, from 15 to 45 degrees, or from 20 to 40 degrees. A handled cup 26 is shown in FIG. 1 covering the opening of the extension spout 22. The cup 26 may be removed from the extension spout 22 and used to measure and pour a selected amount of gravel (not shown) into the extension spout 22 of the simulator 10 during a gravel impact damage simulation. The handled cup 26 may be re-positioned over the opening of the extension spout 22 to act as a lid during the simulation. A safety release panel 28 is slidably mounted in a housing 29 below the extension spout 22. Gravel that is loaded into the extension spout 22 may be held in the spout until the safety release panel 28 is pulled away from the housing 29, thereby allowing the gravel to drop into the enclosure 12. The safety release panel 28 may optionally be spring loaded to bias the safety release panel 28 toward its closed position within the housing 29.

Figure 4:
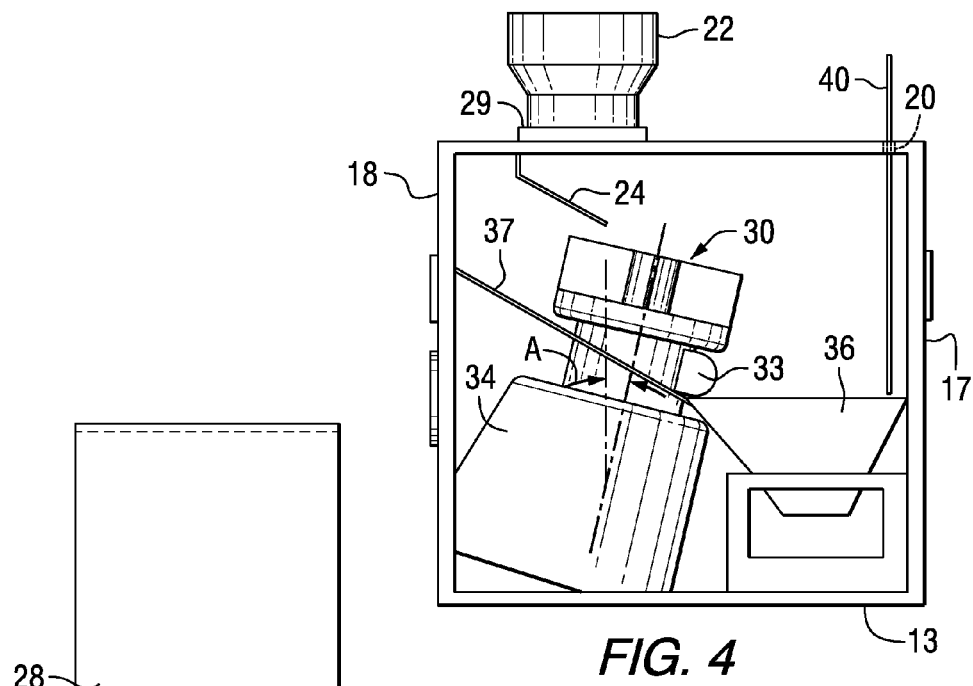
FIG. 4 is a side view of the gravel impact damage simulator of FIG. 1, with its side removed to reveal the internal components thereof.
Figure 5:
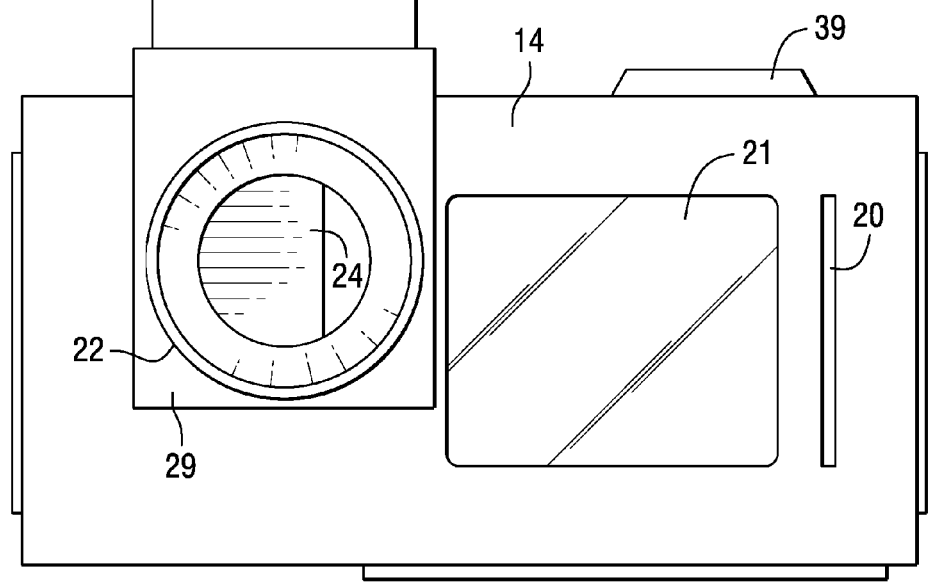
FIGS. 5 and 6 are top views of the gravel impact damage simulator of FIG. 1.
Figure 6:
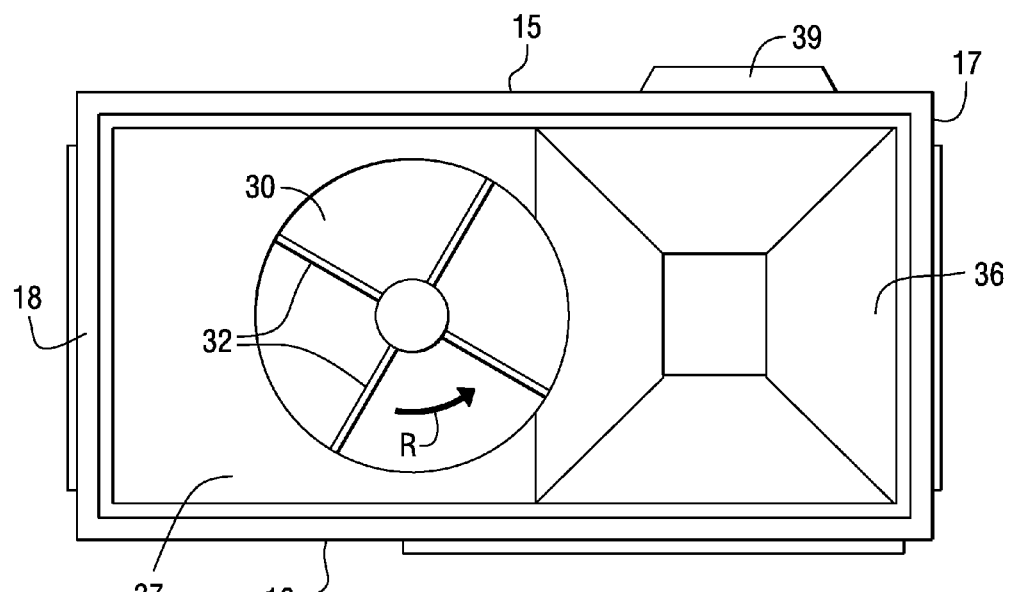

As shown in FIGS. 1, 4 and 6, a rotatable impeller 30 is provided inside the enclosure 12. The rotatable impeller 30 includes multiple paddles 32 extending upwardly therefrom. Although four paddles 32 are shown in the figures, it is to be understood that the rotatable impeller 30 may have any other suitable number of paddles. Furthermore, although each paddle 32 shown in the figures has a generally rectangular shape, any other suitable shape may be used. As shown in FIGS. 1 and 6, the impeller 30 may rotate in the direction R. Although a counterclockwise rotation R direction is shown, it is to be understood that clockwise rotation may alternatively be used.

The angled baffle 24 is used to direct the gravel toward the underlying rotatable impeller 30. While the angled baffle 24 shown in the figures comprises a planar sloped surface, it may alternatively have one or more side walls to help direct the gravel to a desired location in relation to the underlying impeller 30. For example, the angled baffle 24 may have a side wall that directs the gravel toward the side of the impeller 30 that has the paddles 32 rotating toward the end wall 17

The rotatable impeller 30 is driven by an electric motor 34 connected to a power source by an electric power cord 35. The electric motor 34 may be of any known type and can be operated at any desired speed. For example, the electric motor 34 may be operated at 1,600 rpm. The electric motor 34 may have a constant or variable rotational speed. A protective shield 33 extends from an upper part of the housing of the motor 34 in order to prevent possible damage from the impact of gravel during operation of the simulator 10. As shown in FIG. 4, the rotational axis of the impeller 30 is oriented at an offset angle A from the vertical direction. In certain embodiments, the offset angle A may typically range from 1 to 45 degrees, for example, from 5 to 30 degrees, or from 10 to 20 degrees.

As shown most clearly in FIGS. 1, 4 and 6, a collection chute 36 is provided within the enclosure 12. The collection chute 36 has four inwardly sloping sidewalls for directing gravel into a collection container 38 positioned below the collection chute 36. An angled collar plate 37 surrounds the upper portion of the housing of the motor 34 below the rotatable impeller 30. The angled collar plate 37, in combination with the collection chute 36, prevent gravel from contacting the base of the motor 34 and direct the gravel into the collection container 38. An access door 39 permits access to the collection container 38 in order to recover gravel from the simulator 10 after operation thereof. Although the access door 39 is located in the side wall 15 of the simulator 10 in the embodiment shown in the figures, it is to be understood that the access door may be provided at any other suitable location, e.g., in the end wall 17 or the opposite side wall 16. Removal of the collection container 38 from the enclosure 12 may be facilitated by a spring-loaded ejection mechanism (not shown) or the like.

The components of the portable gravel impact simulator 10 may be made of any suitable materials. For example, the enclosure 12, extension spout 22, angled baffle 24, collection chute 36 and angled collar plate 37 may be made of metal or plastic, while the impeller 30 and paddles 32 may be made of plastic or metal. The interior surfaces of the enclosure 12 and/or the extension spout 22, angled baffle 24, collection chute 36 and angled collar plate 37 may optionally be lined with a cushioning or sound absorbing material in order to reduce the noise generated by the simulator during operation.

As shown in FIG. 4, a test panel 40 may be inserted through the slot 20 in a vertical direction adjacent to the end wall 17, e.g., parallel therewith. The test panel 40 is thus positioned in the flight path of the gravel that is projected toward the panel 40, by the rotatable impeller 30. Gravel fed through the inlet opening 22 is projected by the rotating paddle wheel 30 in a generally horizontal direction against the test panel 40. After the gravel impacts the test panel 40, it drops through the collection chute 36 into the collection container 38. Thus, during operation of the simulator 10, a gravel flow path is provided though the extension spout 22, past the safety release panel 28 when it is opened, and onto the angled baffle 24, which directs the gravel toward the rotating impeller 30. The rotating paddles 32 of the impeller 30 strike the gravel to project the gravel along the flow path toward the test panel 40, where the gravel drops into the collection container 38. The size and amount of gravel used in the simulator 10 may be selected as desired. For example, in a typical test run, one-half cup of pea-sized gravel may be poured through the extension spout 22, and the test run may take from 1 to 5 seconds, e.g., 3 seconds.

Figure 7:
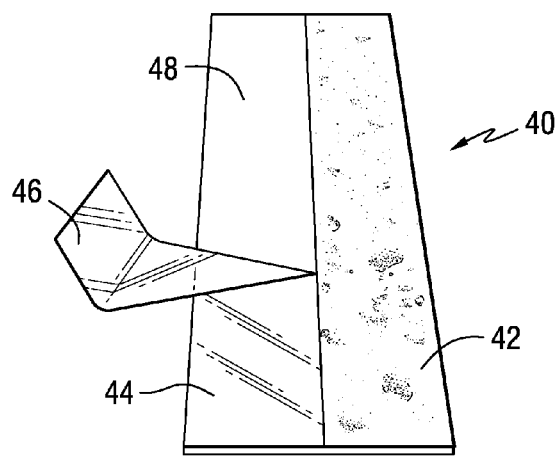
FIG. 7 is an isometric view of a painted test panel having one side covered with a protective film and another side exposed, illustrating the lack of damage on the protected side but significant damage on the exposed side after being subjected to a gravel impact test in a gravel impact damage simulator of the present invention.

FIG. 7 illustrates features of a test panel 40 in accordance with an embodiment of the present invention. The test panel 40 comprises a rectangular sheet of material such as metal or plastic that may be coated with paint. The test panel 40 has an unprotected side 42 in which the painted surface is exposed, as well as a protected side 44 that may be covered by a protective film 46. For example, the test panel 40 may be a metal panel 3.5 inches wide and 10 inches long that has been painted with a color such as black or the like. The protective film 46 on the protected side 44 of the panel may include clear paint protection films, such as those sold by 3M and other manufacturers.

The test panel 40 illustrated in FIG. 7 has been subjected to a gravel impact test in the simulator 10, and a portion of the protective film 46 has been removed from the protected side 44 of the panel to reveal an undamaged painted surface 48 on the protected side 44 of the painted panel. As shown in FIG. 7, the protected side 44 of the panel 40 has not been damaged by the projected gravel, while the unprotected side 42 has suffered significant damage to the paint surface.

In accordance with embodiments of the invention, the portable gravel impact damage simulator 10 includes safety features that prevent unwanted projection of the gravel from the simulator during operation. Such features include the funnel-shaped extension spout 22 at the top of the enclosure 12 through which the gravel may be introduced, the safety release panel 28, the angled baffle 24 positioned below the inlet opening and extension spout 22, and the angled orientation A of the rotatable impeller 30. The extension spout 22 provides a restricted opening through the top 14 of the enclosure 12. The safety release panel 28 holds the gravel within the extension spout 22 until an operator opens the panel 28. This allows time for the operator to place the handled cup 26 over the opening of the extension spout 22 to thereby provide a lid. After the safety release panel 28 is opened, it may be automatically retracted into its closed position, e.g., by a spring biasing mechanism. The size and orientation of the angled baffle 24 further reduces or eliminates the possibility of gravel traveling upward through the inlet opening 22 when the impeller 30 is rotating. Furthermore, the offset angle A of the impeller 30 causes most of the gravel to travel downward and away from the inlet opening 22 when the impeller 30 is rotating. Any gravel that is projected backward or upward during rotation of the impeller 30 is confined within the interior of the enclosure 12 by means of the angled baffle 24, as well as the safety release panel 28 and/or placement of the cup 26 over the opening of the extension spout 22. An additional safety procedure is to first load the gravel into the extension spout 22 with the safety release panel 28 closed, place the cup 26 over the opening of the extension spout 22, turn the motor 32 on, and open the safety release panel 28 to allow the gravel to drop onto the rotating impeller 30. The motor 34 is also protected against damage from gravel impact by the angled collar plate 37 and the protective shield 33.

During operation of the simulator, it is recommended that those in the vicinity should wear eye protection such as safety glasses or goggles.

Whereas particular embodiments of this invention have been described above for purposes of illustration, it will be evident to those skilled in the art that numerous variations of the details of the present invention may be made without departing from the invention as defined in the appended claims.

What is claimed is:

1. A gravel impact damage simulator comprising:
    an enclosure;
    a gravel inlet port extending through a wall of the enclosure, wherein the gravel inlet port comprises an extension spout extending from the wall of the enclosure;
    a motor-driven rotatable impeller below the inlet port within the enclosure, wherein the rotatable impeller has an axis of rotation that is offset at an angle measured from a vertical direction;
    a downwardly angled baffle positioned in a gravel flow path between the gravel inlet port and the rotatable impeller; and
    a test panel slot through a wall of the enclosure structured and arranged to receive a test panel to be positioned in the gravel flow path.

2. The gravel impact damage simulator of claim 1, wherein the wall of the enclosure though which the inlet port extends is a top wall of the enclosure.

3. The gravel impact damage simulator of claim 2, wherein the extension spout extends upwardly from the top wall of the enclosure and has a height that is at least as large as a diameter of the inlet port.

4. The gravel impact damage simulator of claim 1, further comprising a safety release panel movable from a closed position blocking the gravel inlet port to an open position allowing the gravel to flow through the inlet port.

5. The gravel impact damage simulator of claim 4, wherein the safety release panel is located adjacent to a bottom of the extension spout and is slidable in a horizontal direction to move the safety release panel from its closed to open positions.

6. The gravel impact damage simulator of claim 1, wherein the rotatable impeller comprises multiple paddles.

7. The gravel impact damage simulator of claim 1, wherein the offset angle of the impeller is from 5 to 30 degrees.

8. The gravel impact damage simulator of claim 1, wherein the angled baffle has a slope of from 20 to 40 degrees measured from a horizontal direction.

9. The gravel impact damage simulator of claim 1, further comprising a lid positionable over an opening of the extension spout.

10. The gravel impact damage simulator of claim 9, wherein the lid is removable and comprises a cup for holding the gravel.

11. The gravel impact damage simulator of claim 1, further comprising a test panel inserted through the test panel slot.

12. The gravel impact damage simulator of claim 11, wherein the test panel is oriented in a vertical direction and is parallel with an end wall of the enclosure.

13. The gravel impact damage simulator of claim 11, wherein the test panel comprises a painted surface and a portion of the painted surface is covered by a protective film.

14. A test panel for use in a gravel impact damage simulator of claim 1.

15. A method of simulating gravel impact damage comprising:
    inserting a test panel in a gravel impact damage simulator, wherein the simulator comprises:
        an enclosure;
        a gravel inlet port extending through a wall of the enclosure, wherein the gravel inlet port comprises an extension spout extending from the wall of the enclosure;
        a motor-driven rotatable impeller below the inlet port within the enclosure, wherein the rotatable impeller has an axis of rotation that is offset at an angle measured from a vertical direction;
        a downwardly angled baffle positioned in a gravel flow path between the gravel inlet port and the rotatable impeller; and
        a test panel slot through a wall of the enclosure receiving the test panel;
    rotating the impeller; and
    introducing gravel through the inlet opening of the enclosure to thereby direct the gravel from the angled baffle toward the rotating impeller and to project the gravel from the rotating impeller toward the test panel.

16. The method of claim 15, wherein the simulator further comprises a safety release panel movable from a closed position blocking the gravel inlet port to an open position allowing the gravel to flow through the inlet port.

17. The method of claim 15, further comprising positioning a lid over an opening of the extension spout.

18. The method of claim 17, wherein the lid comprises a cup that is used to hold the gravel.

19. The method of claim 15, further comprising removing the test panel from the simulator.

20. The method of claim 15, further comprising removing the gravel from the simulator.

* * * * *